United States Patent [19]

Beech, Jr. et al.

[11] Patent Number: 4,720,600
[45] Date of Patent: * Jan. 19, 1988

[54] PRODUCTION OF MIDDLE DISTILLATE RANGE HYDROCARBONS BY LIGHT OLEFIN UPGRADING

[75] Inventors: James H. Beech, Jr., Wilmington, Del.; Hartley Owen, Belle Mead, N.J.; Michael P. Ramage, Moorestown, N.J.; Samuel A. Tabak, Wenonah, N.J.

[73] Assignee: Mobil Oil Corporation, New York, N.Y.

[*] Notice: The portion of the term of this patent subsequent to Oct. 15, 2002 has been disclaimed.

[21] Appl. No.: 699,882

[22] Filed: Feb. 8, 1985

Related U.S. Application Data

[63] Continuation-in-part of Ser. No. 654,348, Sep. 25, 1984, Pat. No. 4,547,612, and a continuation-in-part of Ser. No. 616,376, Jun. 1, 1984, Pat. No. 4,504,691.

[51] Int. Cl.⁴ .............................................. C07C 2/00
[52] U.S. Cl. ............................ 585/330; 585/315; 585/415; 585/510; 585/533
[58] Field of Search ............... 585/415, 315, 330, 533, 585/510

[56] References Cited

U.S. PATENT DOCUMENTS

| | | | |
|---|---|---|---|
| 4,071,574 | 1/1978 | Milstein et al. | 260/676 R |
| 4,433,185 | 2/1984 | Tabak | 585/315 |
| 4,444,988 | 4/1984 | Capsuto et al. | 585/415 |
| 4,450,311 | 5/1984 | Wright et al. | 585/415 |
| 4,456,779 | 6/1984 | Owen et al. | 585/415 |
| 4,456,781 | 6/1984 | Marsh et al. | 585/415 |
| 4,504,691 | 3/1985 | Hsia et al. | 585/519 |
| 4,544,788 | 10/1985 | Daviduk et al. | 585/501 |
| 4,547,612 | 10/1985 | Tabak | 585/533 |

*Primary Examiner*—Asok Pal
*Attorney, Agent, or Firm*—Alexander J. McKillop; Michael G. Gilman; L. G. Wise

[57] ABSTRACT

An oligomerization process is provided for upgrading lower olefins to distillate hydrocarbons, especially useful as high quality jet or diesel fuels. The olefinic feedstock is reacted over a shape selective acid zeolite, such as ZSM-5, to oligomerize feedstock olefins and further convert recycled hydrocarbons. Reactor effluent is fractionated to recover a light-middle distillate range product stream and to obtain gasoline and heavy hydrocarbon streams for recycle.

13 Claims, 5 Drawing Figures

PRODUCTION OF MIDDLE DISTILLATE RANGE HYDROCARBONS BY LIGHT OLEFIN UPGRADING

REFERENCE TO COPENDING APPLICATIONS

This application is a continuation-in-part of U.S. patent application Ser. No. 654,348, filed 25 Sept. 1984, now U.S. Pat. No. 4,547,612; and a continuation-in-part of U.S. patent application Ser. No. 616,376, filed 1 June 1984, now U.S. Pat. No. 4,504,691.

FIELD OF THE INVENTION

This invention relates to a continuous technique for the manufacture of distillate range hydrocarbons, such as jet aircraft engine fuel or kerosene. In particular, it provides a system for operating an olefins conversion plant wherein a oligomerization catalyst, such as shape selective medium pore crystalline zeolite of the ZSM-5 type, is employed for upgrading olefinic feedstocks containing lower alkenes at elevated temperature and pressure.

BACKGROUND OF THE INVENTION

Recent work in the field of olefin upgrading has resulted in a catalytic process for converting lower olefins to heavier hydrocarbons. Particular interest is shown in a technique developed by Garwood, et al., as disclosed in European Patent Application No. 83301391.5, published 29 Sept. 1983, incorporated herein by reference. Distillate range hydrocarbons can be synthesized over ZSM-5 type catalysts at elevated temperature and pressure to provide a product having substantially linear molecular conformations due to the ellipsoidal shape selectivity of certain medium pore catalysts.

Conversion of olefins to gasoline and/or distillate products is disclosed in U.S. Pat. Nos. 3,960,978 and 4,021,502 (Givens, Plank and Rosinski) wherein gaseous olefins in the range of ethylene to pentene, either alone or in admixture with paraffins are converted into an olefinic gasoline blending stock by contacting the olefins with a catalyst bed made up of a ZSM-5 type zeolite. In U.S. Pat. No. 4,227,992 Garwood and Lee disclose the operating conditions for the Mobil Olefin to Gasoline/Distillate (MOGD) process for selective conversion of $C_3^+$ olefins to mainly aliphatic hydrocarbons. In a related manner, U.S. Pat. Nos. 4,150,062 and 4,211,640 (Garwood et al) disclose a process for converting olefins to gasoline components.

In the process for catalytic conversion of olefins to heavier hydrocarbons by catalytic oligomerization using a medium pore shape selective acid crystalline zeolite, such as ZSM-5 type catalyst, process conditions can be varied to favor the formation of hydrocarbons of varying molecular weight. At moderate temperature and relatively high pressure, the conversion conditions favor $C_{10}^+$ aliphatic product. Lower olefinic feedstocks containing $C_2-C_8$ alkenes may be converted; however, the distillate mode conditions do not convert a major fraction of ethylene. A typical reactive feedstock consists essentially of $C_3-C_6$ mono-olefins, with varying amounts of nonreactive paraffins and the like being acceptable components.

It is a main object of this invention to provide a continuous process devised for upgrading olefins to valuable middle distillate fuel product.

It is a further object to provide an operable olefins oligomerization process to maximize production of light and middle distillate product, such as high quality jet fuel having a boiling range of about 165° to 290° C. (330°–550° F.).

SUMMARY OF THE INVENTION

A continuous process has been devised for converting a feedstock comprising lower olefins to form higher hydrocarbons, particularly distillate product. This process includes the methods and means for producing heavy hydrocarbons comprising distillate range compounds having a substantially linear molecular conformation comprising contacting olefinic feedstock in a catalytic reaction zone under oligomerization conditions at moderate reaction temperature and high pressure favorable to formation of high molecular weight aliphatic hydrocarbons with a shape selective medium pore acidic crystalline silicate zeolite catalyst in a reaction zone maintained under low severity conditions to prevent excessive cracking;

recovering oligomerized hydrocarbon effluent containing middle distillate range hydrocarbon product, higher boiling hydrocarbons and lower boiling hydrocarbons;

fractionating the effluent to obtain a distillate range product fraction, a higher boiling liquid fraction, and a lower boiling liquid fraction; and recycling higher and lower boiling liquid streams comprising at least a major portion of the higher and lower boiling liquid fractions for further reaction in the reaction zone;

This technique is particularly useful for producing middle distillate hydrocarbons comprising $C_9$ to $C_{16}$ aliphatic compounds having a substantially linear molecular conformation.

These and other objects and features of the invention will be understood from the following detailed description and drawings.

THE DRAWINGS

DESCRIPTION OF THE PREFERRED EMBODIMENTS

Figure 1:
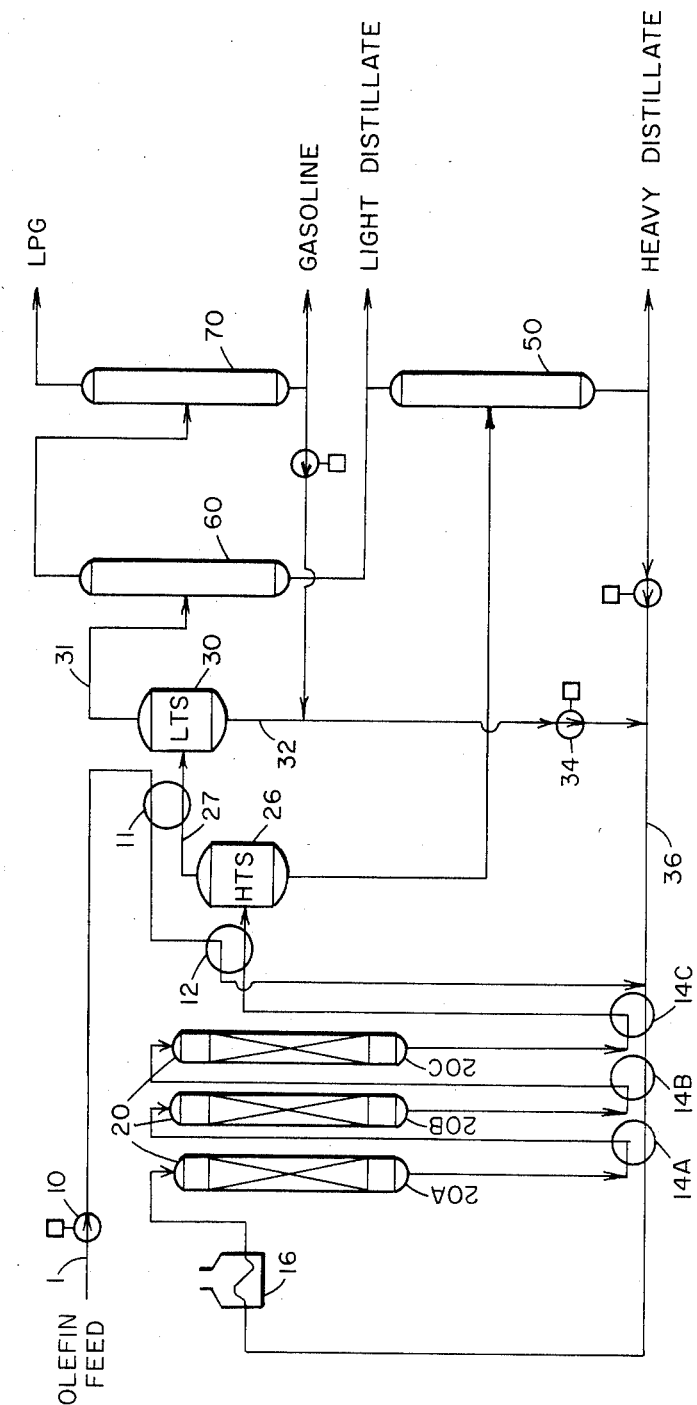
FIG. 1 is a schematic representation of a fixed bed reactor system and product separation system, according to the present invention, showing process flow streams and unit operations.

The oligomerization/polymerization catalysts preferred for use herein include the crystalline aluminosilicate zeolites having a silica to alumina molar ratio of at least 12, a constraint index of about 1 to 12 and acid cracking activity of about 160–200. Representative of the ZSM-5 type zeolites are ZSM-5, ZSM-11, ZSM-12, ZSM-23, ZSM-35 and ZSM-38. ZSM-5 is disclosed and claimed in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,842 for ZSM-23; U.S. Pat.

No. 4,016,245 for ZSM-35 and U.S. Pat. No. 4,046,839 for ZSM-38. The disclosures of these patents are incorporated herein by reference. A suitable shape selective medium pore catalyst for fixed bed is a standard H-ZSM-5 zeolite (silica:alumina ratio=70:1) with alumina binder in the form of cylindrical extrudates of about 1-5 mm. Unless otherwise stated in this description, the catalyst shall consist essentially of this standard ZSM-5, which has an acid cracking value ($\alpha$-value) of about 160-200. Other pentasil catalysts which may be used in one or more reactor stages include a variety of medium pore (~5 to 9 Å) siliceous materials such as borosilicates, ferrosilicates, and/or aluminosilicates disclosed in U.S. Pat. Nos. 4,414,423, 4,417,086, 4,417,087 and 4,417,088, incorporated herein by reference.

Shape-selective oligomerization, as it applies to the conversion of $C_2$-$C_{10}$ olefins over ZSM-5, is known to produce higher olefins up to $C_{30}$ and higher. As reported by Garwood in Intrazeolite Chemistry 23, (Amer. Chem. Soc., 1983), reaction conditions favoring higher molecular weight product are low temperature (200°-260° C.), high pressure (300 psig or greater), and long contact time (0.5-1 WHSV). The reaction under these conditions proceeds through the acid-catalyzed steps of (1) oligomerization, (2) isomerization-cracking to a mixture of intermediate carbon number olefins, and (3) interpolymerization to give a continuous boiling product containing all carbon numbers. The channel systems of ZSM-5 type catalysts impose shape-selective constraints on the configuration of the large molecules, accounting for the differences with other catalysts.

The following model reaction path for propylene is set forth for purposes of explanation, and it should be taken as a theoretical path, as the process is presently understood by workers in the field.

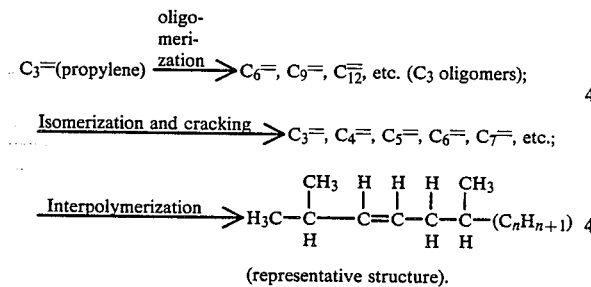

(representative structure).

The desired oligomerization-polymerization products are $C_{10}^+$ substantially linear aliphatic hydrocarbons. As a result of having both forward (polymerization) and reverse (cracking), a continuous molecular weight distribution will occur in the product which can be independent of the carbon number of the starting olefin. For example, Garwood has previously shown, at constant temperature and pressure, virtually identical product distribution for feedstocks of ethylene ($C_2^=$), propylene ($C_3^=$), pentene ($C_5^=$), hexene ($C_6^=$), and decene ($C_{10}^=$). Structurally the final product is influenced by the pore structure of the catalyst. For low carbon number products (i.e., $C_4$, $C_5$) isomer distribution is approximately at equilibrium. For the higher carbon numbers, the structure is primarily a methyl-branched straight olefinic chain, with the maximum cross section of the chain limited by the 5.4×5.6 Angstrom dimension of the largest ZSM-5 pore. At conditions chosen to maximize distillate range products ($C_{10}^+$) the raw aliphatic product is essentially mono-olefinic with 10% or less of the double bond in the alpha position. Overall branching is not extensive, with most branches being methyl at about one branch per four/five carbon atoms.

The flowsheet diagram of FIG. 1 shows the process relationships of the inventive process, depicting the conversion of the $C_3$-$C_6$ rich olefinic intermediate, multi-stage phase separation and recycle. Middle distillate hydrocarbons are recovered by fractionation and may be sent to a conventional hydrotreating unit for product finishing.

General Process Description

The olefinic feedstock supply 1 is normally liquid and can be brought to process pressure by means of pump 10 and preheated by passing sequentially through a series of heat exchange means 11, 12 and reactant effluent exchangers 14C, 14B, 14A and furnace 16 prior to entering the catalytic reactor system 20.

A typical distillate mode first stage reactor system 20 is shown. A multi-reactor system is employed with inter-zone cooling, whereby the reaction exotherm can be carefully controlled to prevent excessive temperature above the normal moderate range of about 200° to 290° C. (400°-550° F.), especially in the final reaction zone. While process pressure may be maintained over a wide range, usually from about 2800 to over 20,000 kPa (400-3000 psia), the preferred pressure is about 4000 to 10,000 kPa (600 to 1500 psia). The feedstock is heated to reaction temperature and carried sequentially through a series of zeolite beds 20A, B, C wherein at least a portion of the olefin content is converted to heavier distillate consitutents. Advantageously, the maximum temperature differential across only one reactor is about 30° C. ($\Delta T = \sim 50°$ F.) and the space velocity (LHSV based on olefin feed) is about 0.1 to 2, preferably about 1.0. The heat exchangers 14A and 14B provide inter-reactor cooling.

In a typical continuous process run under steady state conditions using a standard HZSM-5 catalyst, the average reactor temperature in the series of adiabatic fixed bed reactors is maintained below about 315° C. (600° F.). In order to optimize formation of high molecular weight $C_9^+$ hydrocarbons, effluent temperature from the terminal reactor 20C is kept substantially below about 290° C. (550° F.). Catalyst in the terminal position is preferably the most active in the series, being fresh or regenerated to maintain a high alpha value. By controlling the moderate reaction temperature in the last two beds, undesired cracking of the product $C_9^+$ hydrocarbons is minimized.

The reactor effluent is cooled in exchanges 12 & 14C before fractionation. The effluent fractionation system has two main functions: (1) to provide primary means for separating suitable recycle materials and (2) to provide secondary means for recovering refined product streams of acceptable quality. The primary section is not required to provide streams of clearly defined boiling point components; and, therefore, phase separators in combination with flashing and heat exchange equipment can provide adequate recycle economically. However, the secondary fractionation function requires distinct separation according to molecular weight and boiling point, which usually dictates at least one distillation tower. While the embodiments disclosed herein include operatively connected separators, product splitters, debutanizers, etc., it is within the skill of the art to apply the inventive concept to a variety of effluent separation systems, to provide the required recycle and product streams for a continuous light olefin upgrading system according to the present invention.

The effluent mixture under process pressure or flashed enters a high temperature separator (HTS) 26, wherein higher boiling product is recovered as a liquid rich in $C_{16}{}^+$ hydrocarbons; while vaporizing volatile components of the effluent stream, including the light and intermediate hydrocarbons, such as $C_1$ to $C_{16}$ aliphatics. Preferably, the major portion (e.g. 50% to more than 90 wt %) of $C_{16}{}^+$ hydrocarbon components are contained in the high boiling liquid fraction. Overhead vapor is withdrawn through conduit 27, cooled indirectly by incoming feedstock in exchanger 11 to condense a major amount gasoline range hydrocarbons for recovery in the second phase separation unit 30. This condensed stream is withdrawn through conduit 32 for recycle and pressurized by pump means 34 prior to combining with feedstock in conduit 36. Advantageously, the major portion of $C_5$ to $C_8$ hydrocarbon components boiling below about 165° C. are contained in the liquified lower boiling recycle stream.

Liquid hydrocarbons rich in middle and heavy distillate are recovered from the primary separation zone 26 at process pressure, preferably about 1000 to 1500 kPa (150 to 220 psia) and passed to product splitter tower 50 for secondary fractionation to provide a middle distillate product fraction rich in $C_9$–$C_{16}$ olefins and a $C_{16}{}^+$ heavy distillate stream for recycle or recovery. A vapor overhead stream from the second separation zone 30 is sent directly through conduit 31 to the distillation tower 60 to provide a middle distillate bottoms stream. Gasoline rich overhead from tower 60 is further fractionated in debutanizer tower 70, which provides $C_5$–165° C. olefinic gasoline for additional recycle or product along with $C_3$–$C_4$ rich LPG.

Raw olefinic product may then be hydrotreated in a separate process step (not shown) to provide a paraffinic distillate product meeting jet fuel requirements. Details of a mild hydrogenation treatment may be obtained from U.S. Pat. No. 4,211,640, incorporated by reference, typically using Co or Ni with W/Mo and/or noble metals. The hydrotreated stream may be further fractionated for flash point stabilization.

There are several advantages to the process design. The lower boiling range hydrocarbon recycle consists essentially of $C_5$–$C_8$ hydrocarbons, with minor amounts of $C_4{}^-$ components. This recycle material preferably includes at least 50% of the $C_5$ to $C_8$ hydrocarbons from the reactor effluent. Having a relatively high heat capacity, it provides a good heat sink without diminishing feedstock olefin partial pressure and thereby maintains a high olefin partial pressure at reactor inlet. The liquid recycle is economically repressurized by pumping, which requires modest power consumption.

Typical distillate mode oligomerization operations are conducted over a fixed bed of HZSM-5/alumina extrudate catalyst using the techniques described in U.S. Pat. No. 4,456,779 (Owen, et al.), U.S. Pat. No. 4,433,185 (Tabak), and U.S. Pat. No. 4,547,612, incorporated herein by reference. Reactor sequencing and catalyst regeneration are known in the art.

Figure 2:
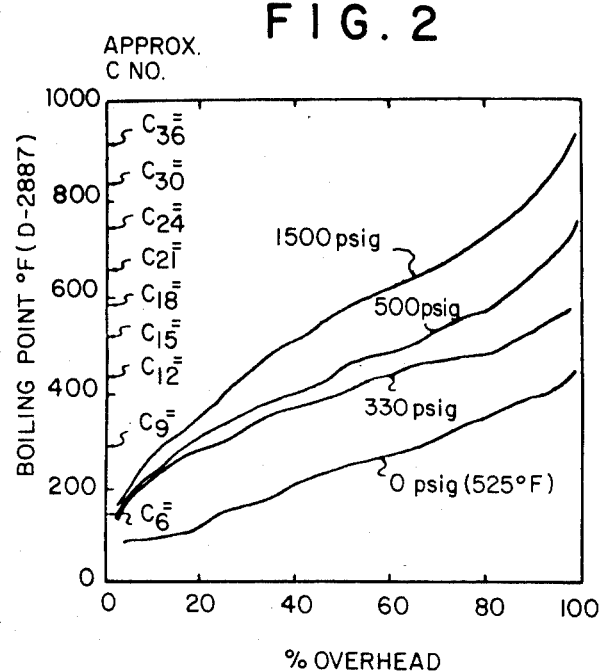
FIG. 2 is a graphic plot showing product distribution for a series of propylene conversion runs at various pressures.

In order to demonstrate the effect of pressure on the process, propylene is reacted at 204° C. and 0.4 WHSV over HZSM-5 in an isothermal reaction zone. FIG. 2 shows a correlation between boiling range of liquid product from 2400 to 10,400 kPa, with a low pressure run (274° C.) plotted for comparison. Propylene conversion is essentially complete at 204° C. under these conditions, and the liquid product includes all carbon numbers from $C_6$ to about $C_{36}$.

Figure 3:
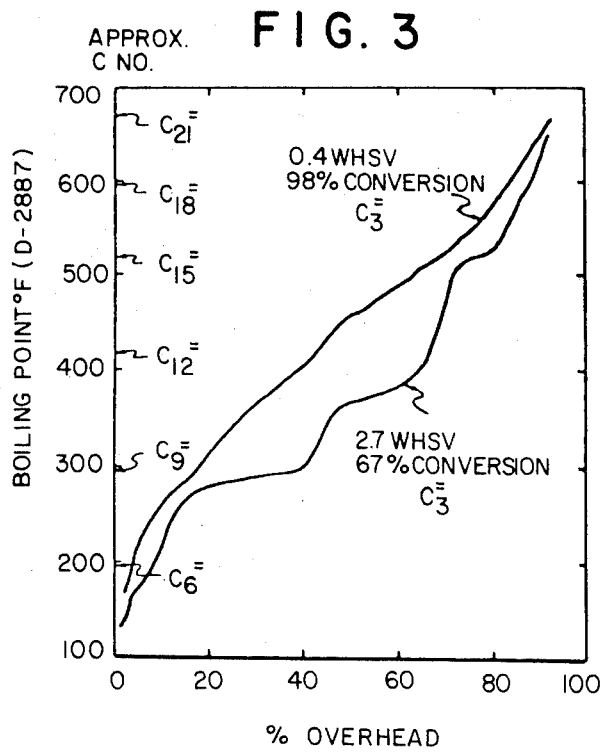
FIG. 3 is a graphic plot of propylene conversion over HZSM-5 at a different space velocities.

In FIG. 3, the effect of contact time is depicted by comparing two runs using propylene feed at 204° C. and 3600 kPa. The liquid boiling plateaus in the higher space velocity run (2.7 WHSV) show evidence of oligomers, corresponding to the trimer, tetramer and pentamer of propylene formed at 67% conversion during short residence. This contrasts with the relatively smooth curve of a longer contact time (0.4 WHSV). The preferred operation with space velocity less than 1 provides essentially complete conversion of $C_3$–$C_{10}$ feedstock. It is a characteristic of the reaction path that the liquid product boiling point curve for propylene is substantially similar to that of a $C_{10}$ (1-decene) feed, at low space velocity (0.1 to 0.5), 277° C. (530° F.) reaction temperature. This suggests that the two widely different charge olefins undergo a common intermediate stage.

Figure 4:
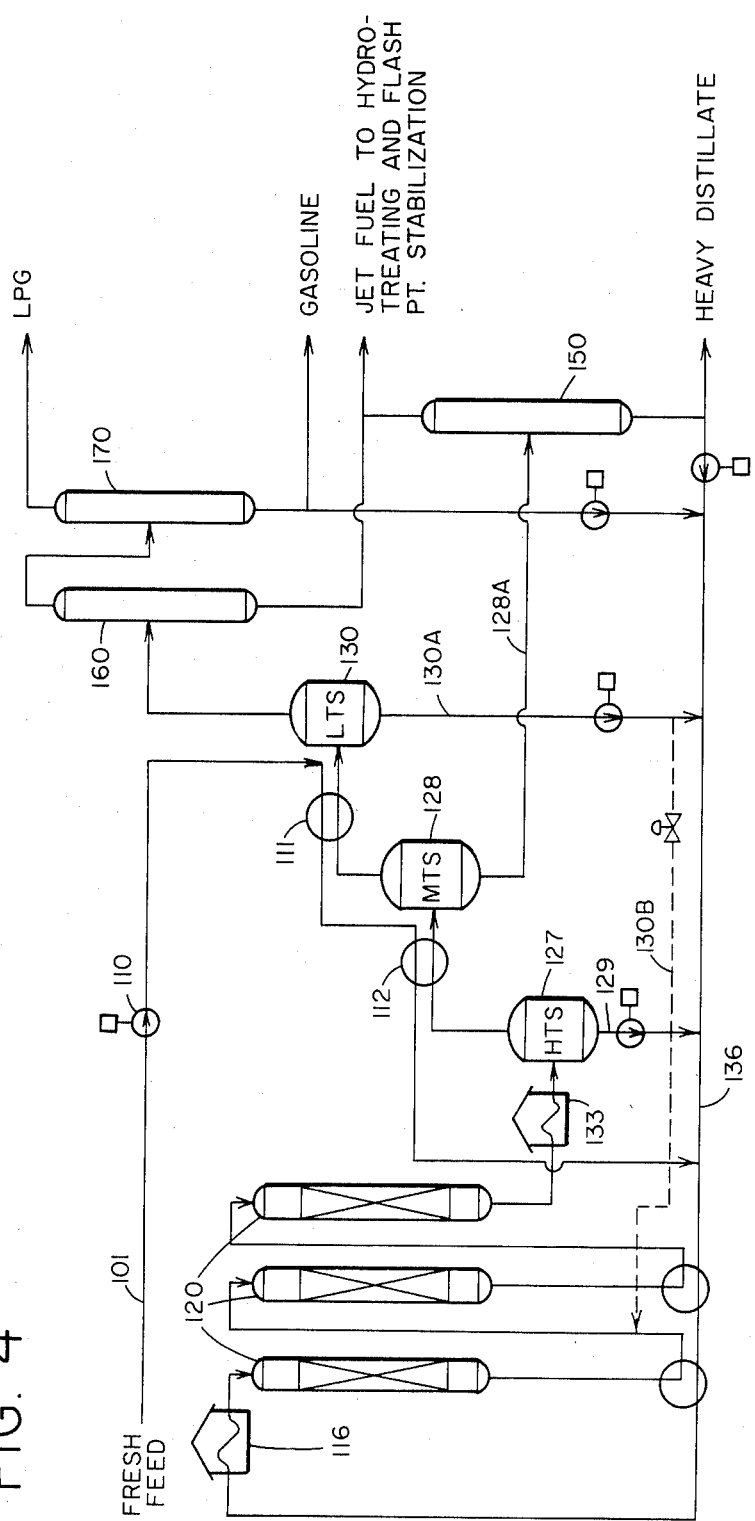
FIG. 4 is a schematic process diagram of an alternative embodiment of the invention.

An alternate embodiment of the inventive process is depicted in FIG. 4, which is a flow sheet for a continuous olefins upgrading plant employing a fixed bed catalytic reactor. Simplified effluent fractionation and recycle streams are shown schematically, with reactor transfer and other details being omitted. Referring to FIG. 4, fresh olefinic feed 101 is pressurized, preheated via exchangers 111, 112, combined with recycle 136 and heated in furnace 116 to reaction temperature. This stream is passed over standard ZSM-5 catalyst in a series of continuous downflow vertical fixed bed reactors 120. The average reactor temperature is incrementally decreased from about 315° C. (600° F.) to 260° C. (500° F.), thereby favoring cracking in the first reactor and oligomerization in the last reactor. A series of high, middle and low temperature phase separators 127, 128, 130 are employed to recover a high boiling liquid recycle stream 129 and a middle distillate-rich liquid product stream 128A, which is passed to distillation tower 150 for splitting into heavy distillate (290° C.+) and light distillate streams. The light distillate may be further treated by hydrogenation and flash point stabilization in a known manner. Gasoline and LPG are recovered by fractionating the overhead vapor from the low temperature separator, from which another recycle stream 130A is taken, which stream is rich in $C_5$ to $C_8$ hydrocarbons. Optionally the light hydrocarbon recycle from low temperature separator 130 may be sent to the low temperature reactor(s) via conduit 130B, bypassing the higher temperature first reactor and thereby avoiding substantial cracking.

In the following examples the average reactor temperature is maintained within the range of 205° to 290° C. (400° to 550° F.), and a space velocity (WHSV based on feed olefin) of about 0.6 to 1.0. Three different operating pressures are employed in successive continuous runs at about 4200 kPa (600 psig), 5600 kPa (800 psig) and at 10400 kPa (1500 psig). Under these conditions, a feedstock consisting of 10.7 weight percent propane, 27 wt % propylene, 26.2 wt % isobutane and 36.1 wt % butylene is converted.

Figure 5:
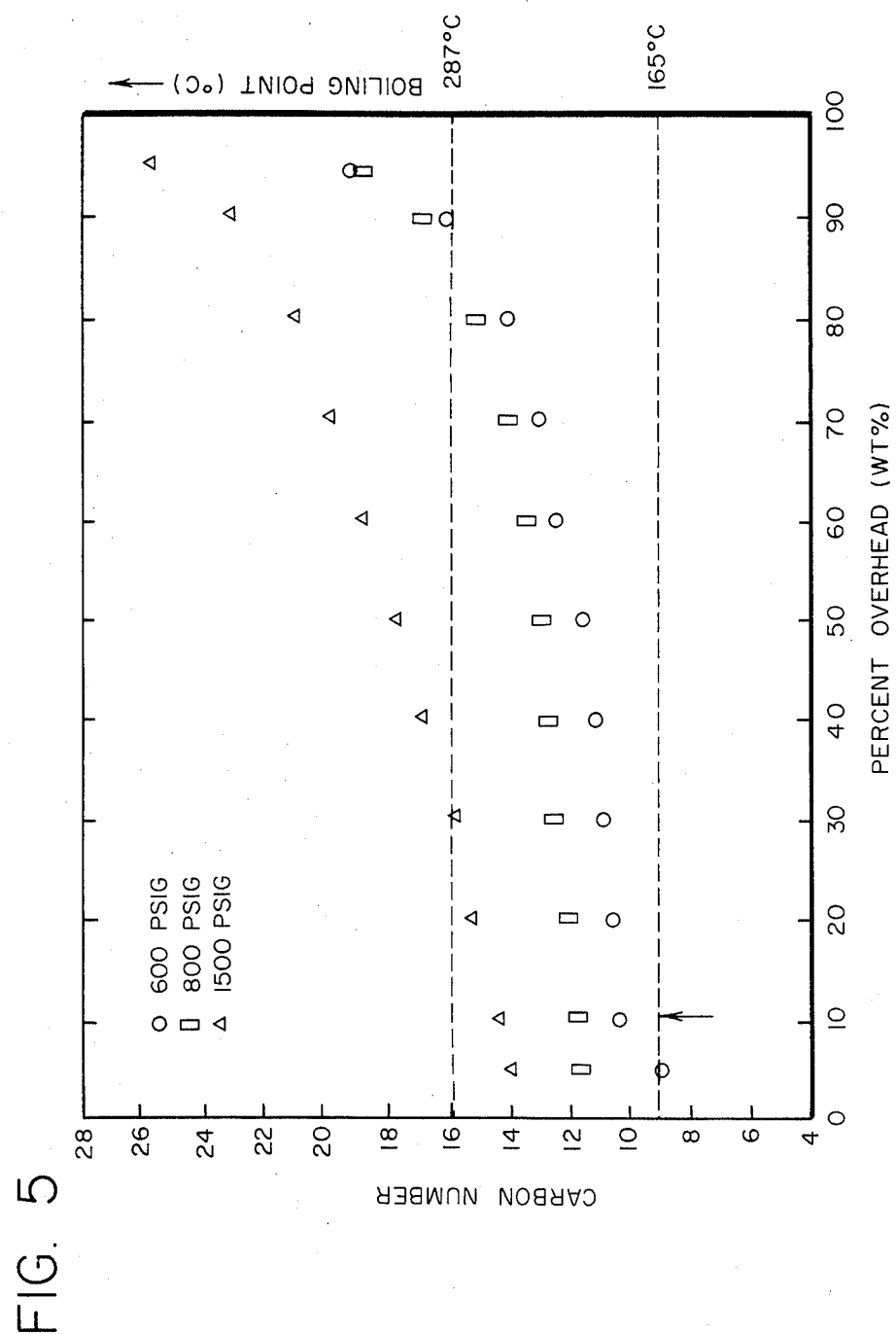
FIG. 5 is a graphic plot of product distribution by carbon number at various pressures.

In FIG. 5, the results of the three runs are plotted to show the product distribution in the reactor effluent, employing gasoline recycle. Optimum jet fuel distillate hydrocarbons are produced in the $C_9$ to $C_{16}$ range, corresponding to a normal boiling point of about 165° C. to 290° C. When the higher boiling 290°+C. hydrocarbons are reprocessed under the same reaction conditions a single pass conversion run yields an average increase of about 23 wt. % to light distillate (165°-290° C.) and 8 wt. % $C_5$-165° C. gasoline range components in the effluent. The product distribution of reprocessed 290° +C. hydrocarbons is shown in Table I.

TABLE I

| Yield from Reprocessed Heavy Distillate, 290°+ C. (550° F.+) | | | | |
|---|---|---|---|---|
| DAYS ON STREAM | 6 | 7 | 8 | 9 |
| OPERATING CONDITIONS | | | | |
| AVE. REAC. TEMP., F. | 500 | 520 | 541 | 561 |
| REAC. PRESS., PSIG | 600 | 600 | 600 | 600 |
| LHSV, (TOTAL) | 1.00 | 1.00 | 1.00 | 1.00 |
| WHSV, (TOTAL) | 1.35 | 1.35 | 1.35 | 1.35 |
| PRODUCT DISTRIBUTION (WT %) | | | | |
| C4 | 0.61 | 0.89 | 1.27 | 1.63 |
| C5+–330F | 6.74 | 7.72 | 7.40 | 9.17 |
| 330F–550F | 24.90 | 23.84 | 22.83 | 21.80 |
| 550F+ | 67.74 | 67.55 | 68.50 | 67.40 |

Typical product specifications for jet fuels are given below.

TABLE II

| Jet Fuel Volatility Specifications | | | | |
|---|---|---|---|---|
| | JP4 (MIL-T-5624L) | JP5 (MIL-T-5624L) | JP7 (MIL-T-38219) | JET A |
| 10% BP (D86), °F. | NS | 401 (max) | 385 (min) | 400 (max) |
| 90% BP (D86), °F. (max) | 473 | NS | 500 | NS |
| End Point (D86), °F. (max) | 518 | 554 | 550 | 572 |
| Flash Point, °F. (min) | NS | 140 | 140 | 100 |

Various modifications can be made to the system, especially in the choice of equipment and non-critical processing steps. While the invention has been described by specific examples, there is no intent to limit the inventive concept as set forth in the following claims.

What is claimed is:

1. A continuous process for producing heavy hydrocarbons comprising distillate range compounds having a substantially linear molecular conformation from lower olefins, comprising:
   contacting olefinic feedstock in a catalytic reaction zone under oligomerization conditions at moderate reaction temperature and high pressure favorable to formation of high molecular weight aliphatic hydrocarbons with a shape selective medium pore acidic crystalline silicate zeolite catalyst in a reaction zone maintained under low severity conditions to prevent excessive cracking;
   recovering oligomerized hydrocarbon effluent containing middle distillate range hydrocarbon product, higher boiling hydrocarbons and lower boiling hydrocarbons;
   fractionating the effluent to obtain a distillate range product fraction, a higher boiling liquid fraction and a lower boiling liquid fraction; and
   recycling higher and lower boiling liquid streams comprising at least a major portion of the higher and lower boiling liquid fractions for further reaction in the reaction zone.

2. The process of claim 1 wherein the catalyst comprises HZSM-5 and wherein the higher boiling stream comprises at least 90 wt % of hydrocarbons boiling above 290° C.

3. The process of claim 2 wherein the oligomerization is conducted at a pressure of at least 2800 kPa.

4. The process of claim 2 wherein the middle distillate product has a boiling range of about 165° C. to 290° C.

5. The process of claim 4 wherein the major portion of $C_6$ to $C_8$ hydrocarbon components are contained in the lower boiling recycle stream, and the major portion of $C_9$ to $C_{16}$ hydrocarbon components are recovered with the distillate product stream.

6. The process of claim 5 wherein the feedstock and recycle streams are combined under process pressure, heated to reaction temperature and passed through a multi-zone reactor system comprising a series of operatively connected fixed bed adiabatic catalytic reactors, with inter-reactor cooling to maintain the average reaction temperature in the reactor beds below about 290° C.

7. The process of claim 6 wherein the weight hourly space velocity is about 0.5 to 2.0, based on fresh feedstock olefins, and wherein the feedstock olefins consist essentially of $C_3$ to $C_6$ mono-olefins.

8. In the continuous process for upgrading lower olefin feedstock to higher hydrocarbons including the steps of combining olefinic feedstock with a pressurized liquid diluent stream comprising $C_5$+ olefins, contacting the diluted feedstock with a shape selective medium pore acid zeolite catalyst under reaction conditions at moderate temperature in a pressurized reactor system comprising a series of catalytic reactor beds to convert olefins and recover reactor effluent at reaction conditions; the improvement which comprises:
   incrementally decreasing reactor temperature from a first reactor bed in the series to last reactor bed to promote oligomerization in the last reactor bed;
   separating reactor effluent in a primary phase separation zone to vaporize light and middle distillate hydrocarbon components into a first vapor phase stream and recover from the primary separation zone a heavy liquid recycle stream, said heavy liquid stream containing at least 50% of those $C_{16}$+ hydrocarbons recovered in the reactor effluent;
   passing the heavy hydrocarbon recycle stream to said first reactor bed, maintained under conditions to degrade the heavy hydrocarbons;
   condensing a light portion of the first vapor phase stream by cooling and recovering from a secondary phase separating zone the dominant portion of a light olefinic recycle stream for further reaction in a lower temperature serial reactor bed to promote oligomerization, said light recycle stream comprising a major portion of $C_6$ to $C_8$ hydrocarbons recovered in the reactor effluent; and
   recovering an intermediate liquid product stream from the secondary separation zone to obtain a distillate product stream consisting essentially of substantially linear $C_9$-$C_{16}$ aliphatic hydrocarbons.

9. The process of claim 8 wherein the catalyst comprises a silicate zeolite having a silica to alumina mole ratio of at least 12 to 1 and a constraint index of about 1 to 12.

10. The process of claim 9 wherein the catalyst comprises HZSM-5, the feedstock olefin comprises a major amount of propylene and butylene.

11. The process of claim 10 wherein feedstock comprising a major amount of $C_3$-$C_6$ olefin is combined with the olefinic recycle stream in a ratio of at least about 0.5 moles of recycle per mole of feedstock olefin and contacted with a fixed bed of acid aluminosilicate zeolite catalyst having a constraint index of about 1 to 12 at a reaction temperature of about 200° C. to 290° C. at process pressure of about 2800 to 20,000 kPa and at a weight hourly space velocity not greater than about 2 to convert a major amount of feedstock olefin.

12. A process of claim 8 further comprising the step of hydrotreating said distillate product stream.

13. A continuous process for upgrading lower olefin feedstock to higher hydrocarbons, comprising the steps of combining olefinic feedstock with a pressurized olefinic recycle stream, contacting the feedstock and recycle with a shape selective medium pore acid zeolite catalyst under reaction conditions at moderate temperature in a pressurized reactor zone to convert feedstock and recycled olefins recovering reactor effluent comprising $C_6$–$C_8$ lower olefins, $C_9$–$C_{16}$ light distillate hydrocarbons and heavy liquid hydrocarbons;

separating reactor effluent to recover a first vapor phase stream and recover a heavy liquid recycle stream, said heavy liquid recycle stream containing a major portion of hydrocarbons in the reactor effluent normally boiling above 290° C.;

condensing a portion of the first vapor phase stream by cooling and recovering the dominant portion of $C_9$ to $C_{16}$ light distillate and an olefinic light hydrocarbon recycle stream for combining with the feedstock, said light recycle stream comprising $C_6$–$C_8$ low boiling hydrocarbons recovered in the reactor effluent; and further fractionating the light distillate stream to obtain a product stream consisting essentially of substantially linear $C_9$ to $C_{16}$ aliphatic hydrocarbons.

* * * * *